(12) United States Patent
Haj-Ahmad (10) Patent No.: US 10,876,105 B2
(45) Date of Patent: *Dec. 29, 2020

(54) METHODS FOR EXTRACELLULAR VESICLE ISOLATION AND SELECTIVE REMOVAL

(71) Applicant: Norgen Biotek Corp., Thorold (CA)

(72) Inventor: Yousef Haj-Ahmad, St. Catharines (CA)

(73) Assignee: Norgen Biotek Corp., Ontario (CA)

( * ) Notice: Subject to any disclaimer, the term of this patent is extended or adjusted under 35 U.S.C. 154(b) by 108 days.

This patent is subject to a terminal disclaimer.

(21) Appl. No.: 16/190,402

(22) Filed: Nov. 14, 2018

(65) Prior Publication Data

US 2019/0078078 A1    Mar. 14, 2019

Related U.S. Application Data

(62) Division of application No. 15/147,969, filed on May 6, 2016, now Pat. No. 10,160,964.

(60) Provisional application No. 62/160,647, filed on May 13, 2015.

(51) Int. Cl.
C12N 15/10        (2006.01)

(52) U.S. Cl.
CPC .......... *C12N 15/1006* (2013.01); *C12N 15/10* (2013.01)

(58) Field of Classification Search
CPC .............................. C12N 15/1006; C12N 15/10
See application file for complete search history.

(56) References Cited

U.S. PATENT DOCUMENTS

| | | |
|---|---|---|
| 6,177,278 B1 | 1/2001 | Haj-Ahmad |
| 6,291,248 B1 | 9/2001 | Haj-Ahmad |
| 7,026,453 B2 | 4/2006 | Haj-Ahmad |
| 7,431,842 B2 | 10/2008 | Haj-Ahmad |
| 8,063,199 B2 | 11/2011 | Haj-Ahmad |
| 2012/0021407 A1 | 1/2012 | Haj-Ahmad |
| 2013/0273544 A1 | 10/2013 | Vlassov et al. |
| 2013/0337440 A1 | 12/2013 | Antes et al. |
| 2014/0255271 A1 | 9/2014 | Haj-Ahmad |

OTHER PUBLICATIONS

Cvjetkovic, Aleksander, et al., The influence of rotor type and centrifugation time on the yield and purity of extracellular vesicles, Journal of Extracellular Vesicles, vol. 3, No. 23111 (2014) (http://dx.doi.org/10.3402/jev.v3.23111).

Thery, Clotilde, et al., Isolation and Characterization of Exosomes from Cell Culture Supernatants and Biological Fluids, Current Protocols in Cell Biology, 3.22.1-3.22.29 (2006).

ExoQuick-TC™ Exosome Precipitation Solution User Manual, Ver. 5-2013-02-21.

Total Exosome Isoliation (from urine), Invitrogen by Life Technologies, Publication No. MAN0008310, Rev. 1.0.

Abdalla et al., Rapid and Non-Phenol extraction of circulating and exosomal RNA from bodily fluids, ResearchGate, Norgen Biotek Corp., (Year: 2012).

*Primary Examiner* — Taeyoon Kim
*Assistant Examiner* — Tiffany M Gough
(74) *Attorney, Agent, or Firm* — Coats & Bennett PLLC (57) ABSTRACT

Disclosed is a method for the isolation of extracellular vesicles, including exosomes, from a liquid sample, the method comprising the steps of: adjusting the pH of a liquid sample comprising extracellular vesicles to a preselected, binding pH; contacting the liquid sample with silicon carbide, wherein at the preselected, binding pH, the extracellular vesicles bind to the silicon carbide; and eluting the bound extracellular vesicles from the silicon carbide. The liquid samples can comprise bodily fluids. Further disclosed is a method for producing a liquid sample, substantially depleted of extracellular vesicles, including exosomes.

10 Claims, 4 Drawing Sheets

METHODS FOR EXTRACELLULAR VESICLE ISOLATION AND SELECTIVE REMOVAL

CROSS-REFERENCE TO RELATED APPLICATION

This application is a divisional of U.S. patent application Ser. No. 15/147,969 filed May 6, 2016. Applicant claims priority based on U.S. Provisional Patent Application Ser. No. 62/160,647 filed May 13, 2015. The subject matter of these applications is incorporated herein.

FIELD OF INVENTION

The present invention relates to methods for the isolation of extracellular vesicles, including exosomes, from liquid samples, including bodily fluids. The present invention further relates to methods for the production of extracellular vesicle-depleted liquid samples, including serum.

BACKGROUND

There are a number of different types of vesicles released by cells, which are known as extracellular vesicles (EV). It is generally accepted that there are 3 main types of EVs which include apoptotic bodies (50-5,000 nm), microvesicles (100-1000 nm), and exosomes (40-150 nm). Apoptotic bodies are shed from dying cells whereas microvesicles are shed from the plasma membrane of viable cells. Exosomes are of endocrytic origin and are formed intracellularly by inward budding of the membrane of endocytic compartments, which then leads to vesicle-containing endosomes called multivesicular bodies (MVBs). These MVBs will then fuse with the plasma membrane, releasing their internal vesicles (the exosomes) into the extracelluar medium (Cvjetkovic et al. *The influence of rotor type and centrifugation time on the yield and purity of extracellular vesicles*. Journal of Extracellular Vesicles, 3: 23111.2014).

Exosomes are secreted by most cell types including epithelial cells, hematopoietic cells, dendritic cells, B cells, T cells, mast cells, platelets, microglia and some tumor cells. Exosomes can be found in various body fluids including urine, saliva, plasma, serum, amniotic fluid, bronchoalveolar fluid and breast milk.

Increasing evidence has suggested that exosomes play an important role in cell-to-cell signaling. In particular, exosomes have been shown to contain cell-specific proteins, lipids and RNAs, which are transported to other cells, where they can alter function and/or physiology. Depending on the cellular origin, exosomes may contain various cellular proteins including MHC molecules, tetraspanins, adhesion molecules and metalloproteinases. In addition to the exosomal proteins, mRNA and miRNA has been recently reported to be found in exosomes, which has brought the attention of many researchers to explore the role of exosomes. Moreover, it has been shown that these exosomal mRNAs can be translated into proteins by recipient cells and that the exosomal miRNAs are able to modulate gene expression in recipient cells.

Exosomes have been shown to be involved in the pathogenesis of cancer and degenerative diseases. Therefore, analysis of exosomal contents can be potentially used for non-invasive diagnostics of cancer and other disorders.

There are a number of different methods for isolating exosomes. The original and most commonly used method involves multiple centrifugation and ultracentrifugation steps (see Thery et al. *Isolation and Characterization of Exosomes from Cell Culture Supernatants and Biological Fluids*. Unit 3.22, Subcellular Fractionation and Isolation of Organelles, in Current Protocols in Cell Biology, John Wiley and Sons Inc., 2006). There are numerous drawbacks associated with the use of ultracentrifugation for exosome isolation. First, this method is not specific for exosomes and will co-purify larger vesicles, protein aggregates and even ribosomes. In addition, this method is time consuming and labour intensive, as it can involve as many as 5 centrifugation steps, with some of the steps requiring speeds of 100,000×g for several hours. Furthermore, this method requires the use of expensive and specialized ultracentrifuges.

Newer methods have been described, which are based upon immuno-magnetic capture of exosomes using magnetic beads coated with antibodies directed against proteins exposed on exosomal membranes. While these antibody based methods eliminate the need for ultracentrifugation, these methods are not suitable for the purification of large amounts of exosomes and are still quite costly.

Methods based on the use of volume-excluding polymers, such as PEG, have been recently described by a number of different groups (U.S. Pat. Appl. 20130273544, U.S. Pat. Appl. 20130337440). Two such products are ExoQuick (System Biosciences, Mountain View, USA) and Total Exosome Isolation Reagent (Life Technologies, Carlsbad, USA). These polymers work by tying up water molecules and forcing less-soluble components such as extracellular vesicles, as well as proteins out of solution, allowing them to be collected by a short, low-speed centrifugation. While the use of precipitation agents eliminate the need for ultracentrifugation and are less expensive that antibodies and beads, there is still the problem of contamination of the exosomes with protein aggregates and macromolecular complexes.

SUMMARY OF INVENTION

In one aspect, disclosed is a method for the isolation of extracellular vesicles from a liquid sample, the method comprising the steps of: (a) adjusting the pH of a liquid sample comprising extracellular vesicles to a preselected, binding pH; (b) contacting the liquid sample with silicon carbide, wherein at the preselected, binding pH, the extracellular vesicles bind to the silicon carbide; and (c) eluting the bound extracellular vesicles from the silicon carbide.

In an embodiment, the isolated extracellular vesicles comprise exosomes.

In a further embodiment, the liquid sample comprises cell culture media.

In a further embodiment, the liquid sample comprises a biological fluid. The biological fluid can be whole blood, blood serum, plasma, urine, saliva, sputum, breast milk, ascetic fluid, semen, vaginal fluid, amniotic fluid, cerebrospinal fluid, sweat or tears.

In a further embodiment, the silicon carbide is in a slurry format. Step (a) of the method can occur before Step (b), such that pH of the liquid sample is adjusted to the preselected binding pH before contacting the liquid sample with the silicon carbide. Alternatively, Step (b) of the method can occur before Step (a), such that the liquid sample is contacted with the silicon carbide before the pH of the liquid sample is adjusted to the preselected binding pH to affect binding of the extracellular vesicles to the silicon carbide.

In a further embodiment, prior to eluting the bound extracellular vesicles from the silicon carbide, the method may further comprise the step of separating the silicon carbide with the bound extracellular vesicles from the liquid sample. The silicon carbide with the bound extracellular vesicles can be separated from the liquid sample using centrifugation or by gravity settling.

In a further embodiment, the silicon carbide is packed into a solid support column.

In a further embodiment, the preselected, binding pH is about 2 to about 4. In a still further embodiment, the preselected, binding pH is about 3.

In a further embodiment, the preselected, binding pH is about 7 to about 11. In a still further embodiment, the preselected, binding pH is about 8.5.

In a still further embodiment, the bound extracellular vesicles are eluted from the silicon carbide using a low salt buffer having a pH of about 4 to about 7. The isolated extracellular vesicles can have an average diameter of about 40 nm to about 150 nm.

In a further aspect, provided is a method for producing a liquid sample substantially depleted of extracellular vesicles, the method comprising the steps of: (a) adjusting the pH of a liquid sample comprising extracellular vesicles to a preselected, binding pH; (b) contacting the liquid sample with silicon carbide, wherein at the preselected, binding pH, the extracellular vesicles bind to the silicon carbide; (c) separating the silicon carbide with the bound extracellular vesicles from the liquid sample to yield a liquid substantially depleted of extracellular vesicles; and (d) collecting the liquid substantially depleted of extracellular vesicles.

In a further embodiment, the isolated extracellular vesicles comprise exosomes.

In a further embodiment, the liquid sample is depleted of at least 95% of the extracellular vesicles initially present in the liquid sample.

In a further embodiment, the liquid sample comprises a serum for supplementing growth in cell culture.

In a further embodiment, the silicon carbide is in a slurry format. Step (a) of the method can occur before Step (b), such that pH of the liquid sample is adjusted to the preselected binding pH before contacting the liquid sample with the silicon carbide. Alternatively, Step (b) of the method can occur before Step (a), such that the liquid sample is contacted with the silicon carbide before the pH of the liquid sample is adjusted to the preselected binding pH.

In a further embodiment, the silicon carbide is packed into a solid support column.

In a further embodiment, the preselected, binding pH is about 2 to about 4. In a still further embodiment, the preselected, binding pH is about 3.

In a further embodiment, the preselected, binding pH is about 7 to about 11. In a still further embodiment, the preselected, binding pH is about 8.5.

DESCRIPTION

Methods For Isolating Extracellular Vesicles

It has been unexpectedly found that silicon carbide (SiC) can be used to selectively isolate extracellular vesicles, including exosomes, from liquid samples. The extracellular vesicles (e.g. exosomes) isolated using SiC have been found to have the characteristics of true extracellular vesicles, as examined by microRNA markers, as well as examination of the size and structure of the extracellular vesicles. Further, the extracellular vesicles isolated using SiC have been found to have substantially reduced levels of contaminating materials, such as macromolecular complexes, ribosomes and proteins, as compared to extracellular vesicles isolated using prior art methods requiring ultracentrifugation or the use of precipitating agents.

Disclosed are methods for the selective isolation of extracellular vesicles, including exosomes, which are rapid, inexpensive, and do not require the use of specialized equipment (e.g. ultracentrifuges). In one embodiment, disclosed is a method for the isolation of extracellular vesicles, including exosomes, from a liquid sample. The method can comprise the steps of:

adjusting the pH of a liquid sample comprising extracellular vesicles to a preselected, binding pH;
   contacting the liquid sample with SiC, wherein at the preselected, binding pH, the extracellular vesicles bind to the SiC; and
   eluting the bound extracellular vesicles from the SiC.

The disclosed method may be used to isolate extracellular vesicles, including exosomes, from any liquid sample containing extracellular vesicles. The liquid sample may comprise biological fluids, such as but not limited to, whole blood, blood serum, plasma, urine, saliva, sputum, breast milk, ascetic fluid, semen, vaginal fluid, amniotic fluid, cerebrospinal fluid, sweat, tears and cell culture media. The biological fluid may come from any mammal, including humans.

The disclosed method may also be used to isolate extracellular vesicles, including exosomes, from biological tissues. The biological tissues are first lysed and the resulting lysate can be used as the liquid sample. The biological tissue may include, but is not limited to, surgical samples, biopsy samples, tissues, feces, plant tissue, insect tissue and cultured cells.

Depending on the composition of the liquid sample, it may be desirable prior to contacting the liquid sample with the SiC, to remove any cells and/or cellular debris contained in the liquid sample. This can be accomplished, for example, by subjecting the liquid sample to centrifugation or filtration to yield a supernatant that is substantially free of cells and cellular debris.

In a preferred embodiment, the SiC can be provided in a slurry format. The SiC slurry can be prepared with a typical industrial preparation of SiC, which is composed of about 97.8% silicon carbide and small amounts of silicon dioxide, silicon, iron, aluminum and carbon. SiC is available in a variety of grit sizes or grades, with each grade having a different average particle size. The SiC slurry can be prepared using any grade of SiC and an appropriate liquid carrier, such as Phosphate Buffered Saline (PBS) buffers (e.g. 1×PBS, pH 7) and Tris buffers (e.g. 10 mM Tris, pH 7). The SiC can have a grit size between 500-2500 (diameter ca. 1-10 µm), preferably a grit size between 2000-2500 and even more preferably, a grit size of 2000. The SiC slurry can be prepared in various ratios of SiC to liquid carrier, with a preferred ratio being between 30% and 70% (w:v), and even more preferred ratio being 50% (w:v).

The pH of the liquid sample can be adjusted to the appropriate binding pH prior to contacting the liquid sample to the SiC slurry. Alternatively, the pH of the liquid sample can be adjusted to the appropriate binding pH, after the liquid sample has already come into contact with the SiC slurry.

To achieve selective binding of the extracellular vesicles to the SiC, the pH of the liquid sample can be adjusted to a binding pH of between pH 2 and pH 4, more preferably between pH 2.5 and pH 3.5, and even more preferably pH 3. The binding pH can also be between pH 7 and pH 11, more preferably between pH 8 and 10, and even more preferably between pH 8.5 and 9.

The pH of the liquid sample can be adjusted using buffers, acids or bases known in the art. The choice of an appropriate buffer, acid or base will depend on the initial pH of the liquid sample containing the extracellular vesicles. For example, the starting pH of some urine samples can be about pH 4 to pH 6, whereas the pH of plasma can be about pH 7. Having regard to the initial pH of the liquid sample, a person skilled in the art can readily determine the appropriate strength and type of buffer, acid or base for adjusting the pH of the liquid sample and also the appropriate amount to be added to the liquid sample to obtain the desired binding pH. Generally, optimal binding conditions can be achieved through the use of a binding solution comprising a low salt buffer with a strong buffering capacity. Examples of suitable low salt buffers include, but are not limited to, Tris acetate buffers, Tris borate buffers, Tris HCl buffers, or Tris buffers.

Following the binding of the extracellular vesicles to the SiC, the liquid portion of the sample can be separated from the bound SiC. As SiC is known to have a high density (3.21 g/cm$^3$), low speed centrifugation can be employed to pellet the SiC and the bound extracellular vesicles. After centrifugation for a few minutes, the remaining liquid portion can be decanted. The extracellular vesicles can then be eluted from the SiC using an elution solution having a pH between 5 and 7, and more preferably a pH of 6. Carrying out the elution step at a pH between 5 and 7 maximizes the selective elution of the extracellular vesicles, including exosomes, and minimizes co-elution of any contaminating proteins that are bound to the SiC. An elution solution comprising a low salt buffer and having a pH between 5 and 7 can be used. Suitable low salt buffers include, but are not limited to, Phosphate Buffered Saline (PBS), Tris Buffer or TE Buffer. The SiC can be removed from the extracellular vesicle containing eluent, for example, by centrifugation and/or filtration to yield a supernatant containing the purified extracellular vesicles, including exosomes.

The purified extracellular vesicles, including exosomes, may be used in various downstream applications, including isolation of exosomal RNA or isolation of exosomal proteins.

In another preferred embodiment of the method, the SiC can be used in a column format. A SiC slurry as described above, can be packed into a column of any size, from small spin columns all the way to large chromatography columns operating through the use of gravity or pumps. The choice of column size will depend on the volume of the liquid sample to be processed. The pH of the liquid sample comprising the extracellular vesicles can be adjusted to the appropriate binding pH using a suitable buffer, acid or base as described above. The pH adjusted liquid sample can then be introduced into the SiC column. As the liquid sample travels through the SiC column, the extracellular vesicles, including exosomes, contained in the liquid sample will come into contact with the SiC and will selectively bind to the SiC. The bound extracellular vesicles, including exosomes, can be eluted from the SiC by passing an appropriate elution solution, as described through the column and the eluted extracellular vesicles can be collected for downstream applications.

Methods For Producing Liquids Depleted of Extracellular Vesicles

Media for the growth of cultured cells is often supplemented with serum, which is known to contain extracellular vesicles, including exosomes. These exogenous exosomes present in the serum can negatively affect experimental results by interfering with the exosomes being studied in the cell culture, as they will be co-purified with the exosomes being produced by the cell line of interest. Therefore, researchers who are working with cell culture to carry out research involving exosomes often require exosome-free media or serum to ensure that their results are not affected or altered.

Further disclosed are methods for depleting extracellular vesicles, including exosomes, from liquid materials, including cell culture media and serum. Through the use of SiC, extracellular vesicles present in the liquid material can be selectively removed from the liquid material. In contrast to prior art methods for the preparation of cell culture media and serum free of extracellular vesicles (e.g. ultracentrifugation or filtration methods) the disclosed depletion method is rapid, inexpensive, and does not require the use of specialized equipment. Further, the disclosed method may be used to remove extracellular vesicles, including exosomes, from large volumes of cell culture media, serum or other liquid materials.

In one embodiment, disclosed is a method for producing a liquid sample substantially depleted of extracellular vesicles, including exosomes, comprising the steps of:

adjusting the pH of a liquid sample comprising extracellular vesicles to a preselected, binding pH;

contacting the liquid sample with SiC, wherein at the pre-selected, binding pH, the extracellular vesicles bind to the SiC;

separating the SiC with the bound extracellular vesicles from the liquid sample to yield a liquid substantially depleted of extracellular vesicles; and collecting the liquid substantially depleted of extracellular vesicles.

As used herein, a liquid sample that has been depleted of at least 95% of the extracellular vesicles initially present in the liquid sample prior to contacting the liquid sample with SiC is considered to be a "liquid sample substantially depleted of extracellular vesicles".

In a preferred embodiment, the liquid sample to be substantially depleted of extracellular vesicles, including exosomes, may be a serum sample. The serum sample may be selected from any type of serum used to supplement cell culture for cell growth, including but not limited to, fetal bovine serum, horse serum, and fetal calf serum. While the embodiments set out below describe the preparation of serum samples depleted of extracellular vesicles, it will be appreciated that method can be used with other types of liquid samples, including liquid samples comprising other types of bodily fluids and also liquid samples such as cell culture media.

The SiC can be provided as a slurry as described above. The pH of the serum sample can be adjusted to an appropriate binding pH prior to contacting the liquid sample to the SiC slurry. Alternatively, the pH of the serum sample can be adjusted to an appropriate binding pH, after the liquid sample has already come into contact with the SiC slurry.

To achieve selective binding of the extracellular vesicles to the SiC, the pH of the serum sample is adjusted to a binding pH of between pH 2 and pH 4, more preferably between pH 2.5 and pH 3.5, and even more preferably pH 3. The binding pH can also be between pH 7 and pH 11, more preferably between pH 8 and 10, and even more preferably between pH 8.5 and 9.

The pH of the serum sample can be adjusted using buffers, acids or bases known in the art. The choice of an appropriate buffer, acid or base will depend on the initial pH of the serum sample. Having regard to the initial pH of the serum sample, a person skilled in the art can readily determine the appropriate strength and type of buffer, acid or base for adjusting the pH of the serum sample and also the appropriate amount to be added to the serum sample to obtain the desired binding pH. Generally, optimal binding conditions can be achieved through the use of a binding solution comprising a low salt buffer with a strong buffering capacity. Examples of suitable binding buffers include are but not limited to Tris acetate buffers, Tris borate buffers, Tris HCl buffers, or Tris buffers.

Following the binding of the extracellular vesicles to the SiC, the bound SiC can be removed to yield a serum sample substantially depleted of extracellular vesicles. Low speed centrifugation can be employed to pellet the SiC and the bound extracellular vesicles. After centrifugation for a few minutes, the serum sample substantially depleted of extracellular vesicles can be decanted for use in other applications.

In another preferred embodiment of the method, the SiC can be used in a column format. A SiC slurry as described above, can be packed into a column of any size, from small spin columns all the way to large chromatography columns operating through the use of gravity or pumps. The choice of column size will depend on the volume of the serum sample to be processed. The pH of the serum sample, comprising the extracellular vesicles to be depleted, can be adjusted to the appropriate binding pH using a buffer, acid or base as described above. The pH adjusted serum sample can then be introduced into the column. As the serum sample travels through the column, the extracellular vesicles, including exosomes, contained in the serum sample will come into contact with the SiC and will selectively bind to the SiC. The remaining extracellular vesicle-depleted serum that flows through the column can be collected for use in other applications.

Through the use of SiC in either a slurry format or a column format, serum samples can depleted of over 95% of extracellular vesicles initially present in the serum sample. The extracellular vesicle-depleted serum samples can be use in cell culture, and more specifically for growing cultured mammalian cells.

Kits for the Isolation or Depletion of Extracellular Vesicles

In a further embodiment, provided are kits for the isolation of extracellular vesicles, including exosomes, from liquid samples. The kits can be used to carry out the isolation method disclosed herein. Such kits may comprise vessels containing a SiC slurry, a binding solution to adjust the pH of the liquid sample to an appropriate binding pH to bind the extracellular vesicles to the SiC, and an elution solution to adjust the pH in order to specifically release the bound extracellular vesicles from the SiC. The kit may further contain filter columns, which may aid in removing the SiC from the liquid samples following elution of the extracellular vesicles. Alternatively, the kit may comprise SiC columns, vessels containing a binding solution to adjust the pH of the liquid sample to an appropriate binding pH to bind the extracellular vesicles to the SiC, and an elution solution to adjust the pH in order to specifically release the bound extracellular vesicles from the SiC.

In another embodiment, provided are kits for the depletion of extracellular vesicles from liquid samples. The kits can be used to carry out the depletion method disclosed herein. Such kits may comprise vessels containing a SiC slurry and a binding solution to adjust the pH of the liquid sample to an appropriate binding pH to bind the extracellular vesicles to the SiC. The kit may further contain filter columns which may aid in removing the SiC from the liquid samples to produce the substantially extracellular vesicles-depleted sample. Alternatively, the kit may comprise SiC columns and vessels containing a binding solution to adjust the pH of the liquid sample to an appropriate binding pH to bind the extracellular vesicles to the SiC.

Although the invention has been described with reference to illustrative embodiments, it is to be understood that the invention is not limited to these precise embodiments, and that various changes and modification are to be intended to be encompassed in the appended claims.

EXAMPLES

These examples are described for the purposes of illustration and are not intended to limit the scope of the invention.

Example 1

Comparing the Efficiency of SiC Versus Commercially Available Kits in Isolating Extracellular Vesicles, Including Exosomes, from Urine SiC in a slurry format was tested for its ability to isolate exosomes from 5 mL of urine, and the performance of the SiC was compared to two different commercially available exosome precipitation reagents. The SiC slurry was prepared by adding 6.25 grams of SiC (G/S 2500) to 10 mL of 1×PBS (pH 7). Fifteen mL of urine was collected into a conical tube and centrifuged at 200×g (~1,000 RPM) for 10 minutes to remove urine exfoliated cells and debris. The cell-free urine was decanted into a new tube and centrifuged at 1,800×g (~3,000 RPM) for 10 minutes to remove any residual debris or bacterial cells. Five mL of the cell-free urine was transferred to a new tube and 400 µL of the SiC slurry was added to the urine samples. The pH was then adjusted to pH 8.5 using 1M Tris Base (pH 11) to allow for the exosomes to bind to the SiC resin. The sample was mixed by vortexing for 10 seconds and left to stand at room temperature for 10 minutes. The suspension was again mixed well by vortexing for 10 seconds, and then centrifuged for 2 minutes at 2,000 RPM. The supernatant was then discarded. Next, 400 µL of 1×PBS (pH 7) was added to the slurry pellet in order to adjust the pH to 6, and mixed well by vortexing for 10 seconds. The resuspended slurry pellet was then incubated for 10 minutes at room temperature. After incubation, the slurry pellet was mixed well by vortexing for 10 seconds then centrifuged for 2 minutes at 500 RPM. The supernatant containing the eluted exosomes was then transferred to a filter column (0.2 µM pore size) and centrifuged for 1 minute at 6,000 RPM.

Exosomes were also isolated from 5 mL of urine using ExoQuick-TC for Tissue Culture Media and Urine (System Biosciences, Mountain View, USA) and from 5 mL of urine using Total Exosome Isolation Reagent (from urine) (Life Technologies, Carlsbad, USA) according to the manufacturer's recommendations.

Figure 1:
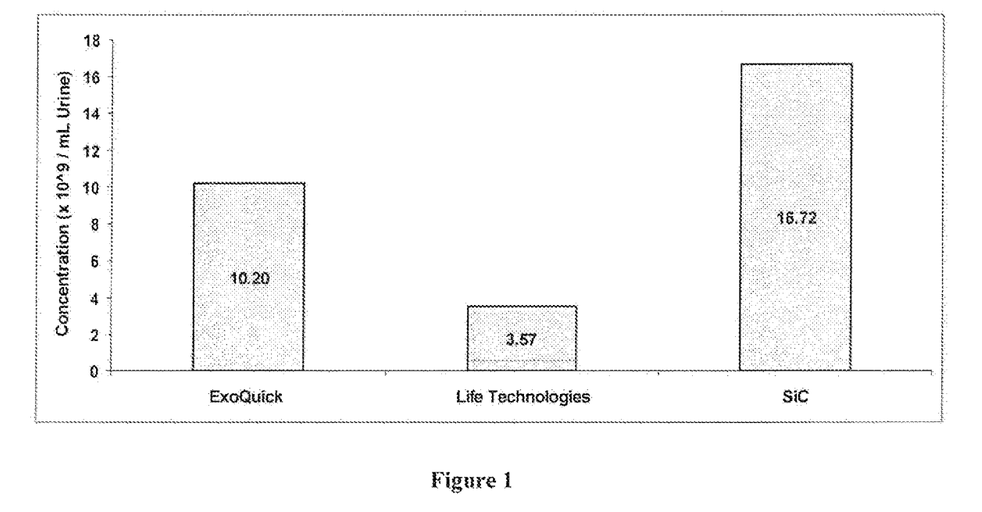
FIG. 1 is a bar graph showing the concentration of exosomes isolated from 5 mL of urine using SiC, ExoQuick-TC for Tissue Culture Media and Urine (System Biosciences, Mountain View, USA) and Total Exosome Isolation Reagent (from urine) (Life Technologies, Carlsbad, USA).
Figure 2:
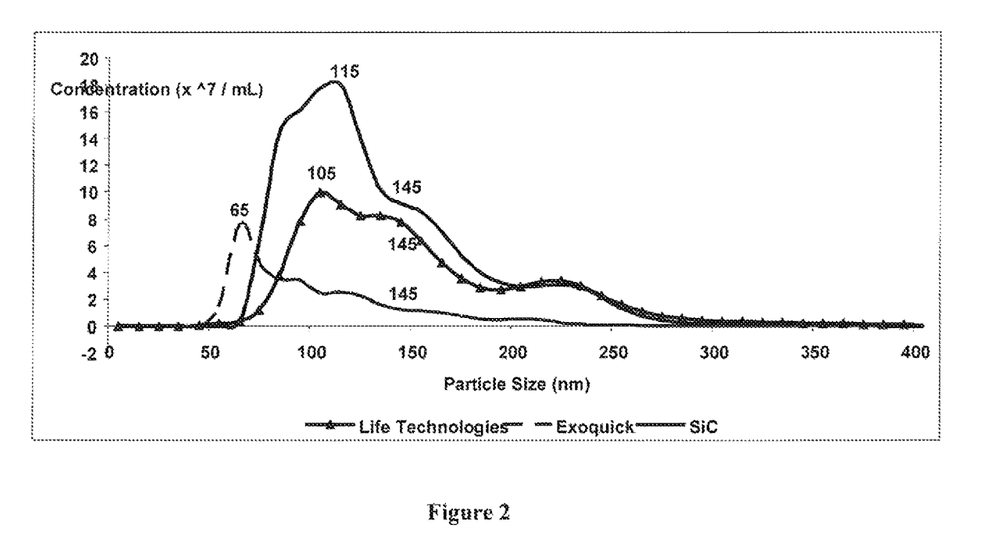
FIG. 2 is a line graph showing the concentration and particle size of exosomes isolated from 5 mL of urine using SiC, ExoQuick-TC for Tissue Culture Media and Urine (System Biosciences, Mountain View, USA) and Total Exosome Isolation Reagent (from urine) (Life Technologies, Carlsbad, USA).

In order to analyze the purified exosomes, the eluted exosomes were visualized using a NanoSight LM10 instrument. The analysis showed that the SiC method isolated the highest amount of exosomes, with a recovery of 16.72×10^9 particles/mL urine, which is higher than both the other methods tested. The graph showing the concentration of exosomes isolated using SiC and the 2 other methods can be seen in FIG. 1. No impurities were found to be contaminating the exosomes purified using SiC, as indicated by the Nanosight analysis. The graph showing the particle size distribution using SiC and the other 2 methods can be seen in FIG. 2. As shown in FIG. 2, the majority of extracellular vesicles isolated by SiC are in the size range of 40-150 nm, which is typical for exosomes.

Example 2

Comparing the Efficiency of SiC Versus Commercially Available Kits in Isolating Extracellular Vesicles, Including Exosomes, from Plasma SiC in a slurry format was tested for its ability to isolate extracellular vesicles, including exosomes, from 1 mL of plasma, and the performance of the SiC was compared to two different commercially available exosome precipitation reagents. The SiC slurry was prepared by adding 6.25 grams of SiC (G/S 2500) to 10 mL of 1×PBS (pH 7). Blood was collected on EDTA or citrate using a standard blood collection tube. The collection tube was centrifuged at 2000 RPM for 15 minutes. The upper plasma fraction was collected and transferred to a fresh tube and centrifuged at 2000 RPM for 10 minutes. The clear supernatant containing the purified plasma was collected. One mL of the prepared plasma was transferred to a tube and 200 µL of the SiC slurry was added to the plasma samples. The pH was then adjusted to pH 8.5 using 1M Tris Base (pH 11) to allow for the exosomes to bind to the SiC resin. The sample was mixed by vortexing for 10 seconds and left to stand at room temperature for 5 minutes. The suspension was again mixed well by vortexing for 10 seconds, and then centrifuged for 2 minutes at 2,000 RPM. The supernatant was then discarded. Next, 200 µL of 1×PBS (pH 7) was added to the slurry pellet in order to adjust the pH to 6, and mixed well by vortexing for 10 seconds. The resuspended slurry pellet was then incubated for 5 minutes at room temperature. After incubation, the slurry pellet was mixed well by vortexing for 10 seconds then centrifuged for 2 minutes at 500 RPM. The supernatant containing the eluted exosomes was then transferred to a filter column (0.2 µM pore size) and centrifuged for 1 minute at 6,000 RPM.

Exosomes were also isolated from 1 mL of plasma using ExoQuick Plasma Prep and Exosome Purification Kit (System Biosciences, Mountain View, USA) and from 1 mL of plasma using Total Exosome Isolation Kit (from plasma) (Life Technologies, Carlsbad, USA) according to the manufacturer's recommendations.

Figure 3:
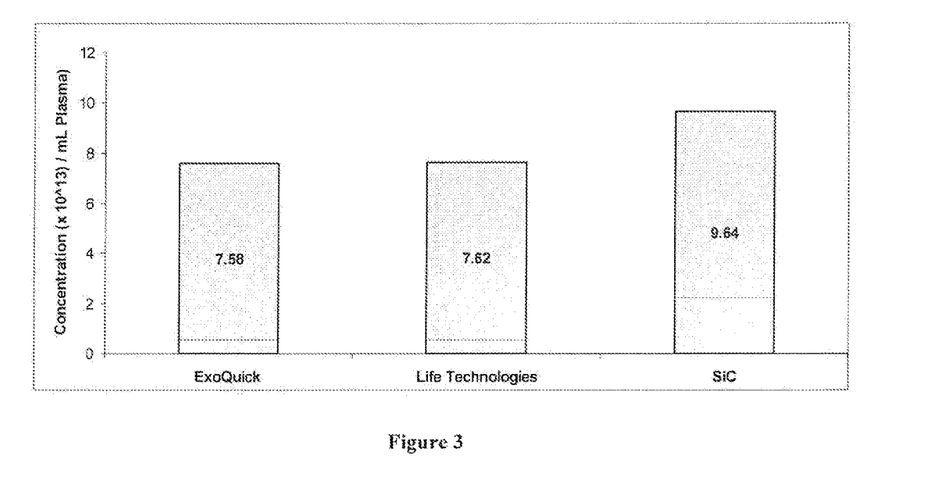
FIG. 3 is a bar graph showing the concentration of exosomes isolated from 1 mL of plasma using SiC, ExoQuick Plasma Prep and Exosome Purification Kit (System Biosciences, Mountain View, USA) and Total Exosome Isolation Kit (from plasma) (Life Technologies, Carlsbad, USA).
Figure 4:
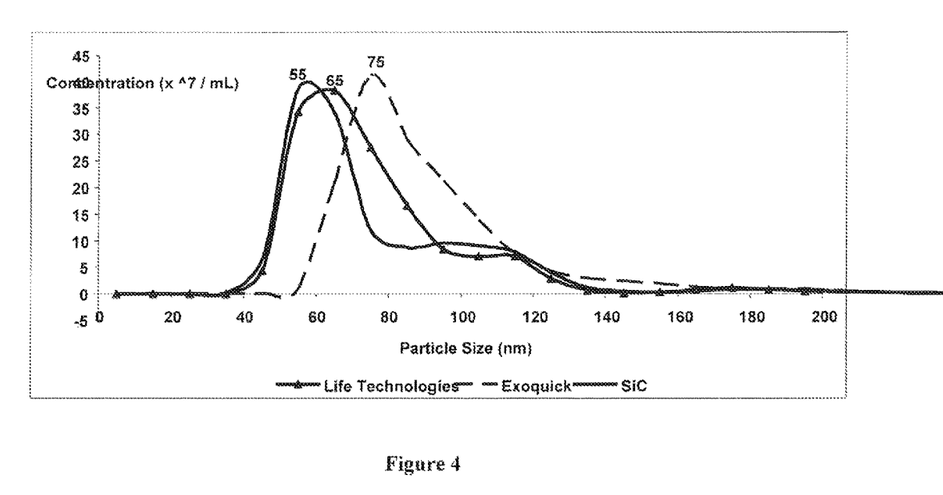
FIG. 4 is a line graph showing the concentration and particle size of exosomes isolated from 1 mL of plasma using SiC, ExoQuick Plasma Prep and Exosome Purification Kit (System Biosciences, Mountain View, USA) and Total Exosome Isolation Kit (from plasma) (Life Technologies, Carlsbad, USA).

In order to analyze the purified exosomes, the eluted exosomes were visualized using a NanoSight LM10 instrument. The analysis showed that the SiC method isolated the highest amount of exosomes, with a recovery of 9.64×10^13 particles/mL of plasma, which is higher than both the other methods tested. The graph showing the concentration of exosomes isolated from 1 mL plasma using SiC and the 2 other methods can be seen in FIG. 3. No impurities were found to be contaminating the exosomes purified using SiC, as indicated by the Nanosight analysis. The graph showing the particle size distribution using SiC and the other 2 methods can be seen in FIG. 4. As shown in FIG. 4, the majority of extracellular vesicles isolated by SiC are in the size range of 40-150 nm, which is typical for exosomes.

Example 3

Comparing the Efficiency of SiC Versus Ultracentrifugation in Isolating Extracellular Vesicles, Including Exosomes, from Urine SiC in a slurry format was tested for its ability to isolate exosomes from 10 mL of urine, and the performance of the SiC was compared to the traditional method of ultracentrifugation. The SiC slurry was prepared by adding 6.25 grams of SiC (G/S 2500) to 10 mL of 1×PBS (pH 7). Ten mL of urine was collected into a conical tube and centrifuged at 200×g (~1,000 RPM) for 10 minutes to remove urine exfoliated cells and debris. The cell-free urine was decanted into a new tube and centrifuged at 1,800×g (~3,000 RPM) for 10 minutes to remove any residual debris or bacterial cells. The remaining cell-free urine sample was transferred to a new tube and 400 µL of the SiC slurry was added to the urine samples. The pH was then adjusted to pH 8.5 using 1M Tris Base (pH 11) to allow for the exosomes to bind to the SiC resin. The sample was mixed by vortexing for 10 seconds and left to stand at room temperature for 10 minutes. The suspension was again mixed well by vortexing for 10 seconds, and then centrifuged for 2 minutes at 2,000 RPM. The supernatant was then discarded. Next, 400 µL of 1×PBS (pH 7) was added to the slurry pellet order to adjust the pH to 6, and mixed well by vortexing for 10 seconds. The resuspended slurry pellet was then incubated for 10 minutes at room temperature. After incubation, the slurry pellet was mixed well by vortexing for 10 seconds then centrifuged for 2 minutes at 500 RPM. After incubation, the slurry pellet was mixed well by vortexing for 10 seconds then centrifuged for 2 minutes at 500 RPM. The supernatant containing the eluted exosomes was then transferred to a filter column (0.2 µM pore size) and centrifuged for 1 minute at 6,000 RPM.

Exosomes were also isolated from urine using traditional ultracentrifugation as outlined in Thery et al. (*Current Protocols in Cell Biology*, 2006). For this procedure, 240 mL of urine was processed and the final exosome pellet was resuspended in 240 µL of 1×PBS (pH 7). Therefore, for analysis of exosomes, 10 µL of the elution was analyzed which would correspond to 10 mL of initial urine input.

Figure 5A:
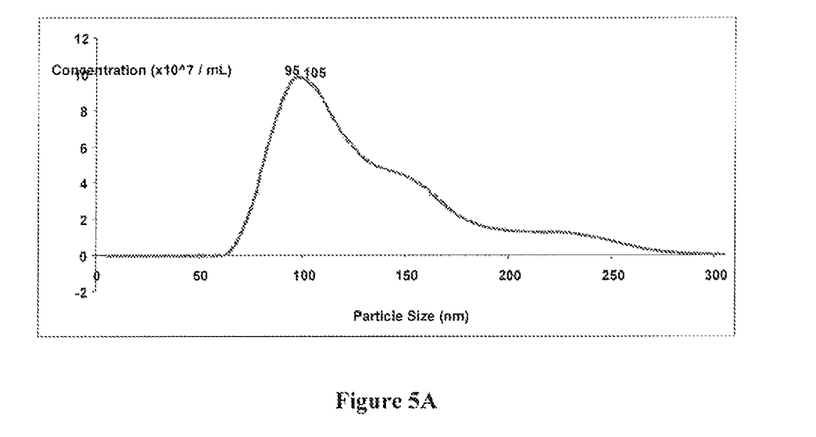
FIG. 5A is a line graph showing the concentration and particle size of exosomes purified from 10 mL of urine using SiC.
Figure 5B:
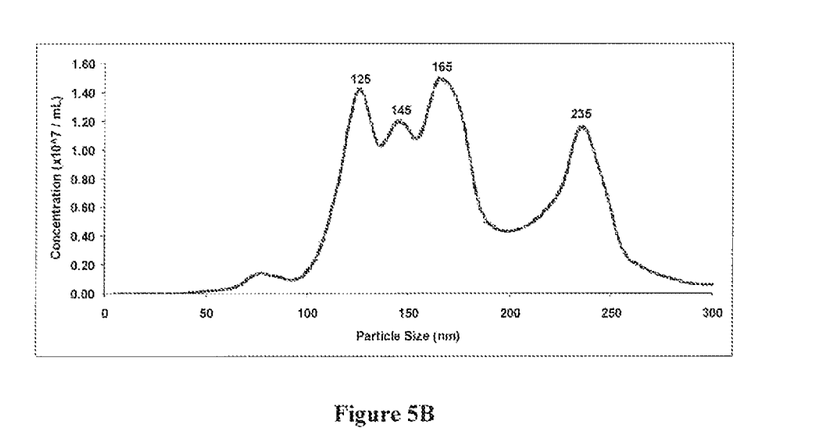
FIG. 5B is a line graph showing the concentration and particle size of exosomes purified from 10 mL of urine using ultracentrifugation.

The purified exosomes were analyzed and visualized using a NanoSight LM10 instrument. The results are show in FIGS. 5A and 5B. The analysis showed that the SiC method (FIG. 5A) isolated exosomes with a recovery of $7.63 \times 10^8$ particles/mL, and the majority of extracellular vesicles isolated are in the size range of 40-150 nm, which is typical for exosomes. In contrast, ultracentriguation (FIG. 5B) purified larger extracellular vesicles, with a size range from 125 nm to 235 nm, with a total recovery of $1.56 \times 10^8$ particles/mL. The larger extracellular vesicles isolated using ultracentrifugation do not correspond to the typical size range of exosomes, indicating that this gold-standard method is not as specific as the use of SiC to purify exosomes.

Example 4

Comparing RNA Recovery From Exosomes Isolated Using SiC Versus Commercially Available Kits SiC in a slurry format was tested for its ability to isolate exosomes from 5 mL of urine, and the performance of the SiC was compared to two different commercially available exosome precipitation reagents. The SiC slurry was prepared by adding 6.25 grams of SiC (G/S 2500) to 10 mL of 1×PBS (pH 7). The exosomes were isolated from 15 mL urine samples using the SiC slurry as described in Example 1 above.

Exosomes were also isolated from 5 mL of urine using ExoQuick-TC for Tissue Culture Media and Urine (System Biosciences, Mountain View, USA) and from 5 mL of urine using Total Exosome Isolation Reagent (from urine) (Life Technologies, Carlsbad, USA) according to the manufacturer's recommendations.

RNA was then purified from the isolated exosomes. For exosomes purified using SiC, the RNA was isolated by adding 300 µL of Lysis Buffer from Norgen Biotek's Plasma/Serum RNA Purification Mini Kit (Cat #55000, Norgen Biotek, Thorold, Canada) and 37.5 µL of Lysis Additive from Norgen Biotek's Fatty Tissue RNA Purification Kit (Cat #36200, Norgen Biotek, Thorold, Canada) to the purified exosomes. This was mixed and then incubated at room temperature for 10 minutes. Next, 500 µL of ethanol was added and mixed well. This was then added to a column containing SiC resin, and centrifuged for 1 minute at 3,300×g (~6,000 RPM). The flowthrough was discarded, and the bound RNA was washed using Wash Solution from Norgen Biotek's Plasma/Serum RNA Purification Mini Kit (Cat #55000, Norgen Biotek, Thorold, Canada) by centrifugation for 30 seconds at 3,300×g (~6,000 RPM). The flowthrough was discarded, and the wash step was repeated 2 more times. After a dry spin, 50 µL of Elution Solution from Norgen Biotek's Plasma/Serum RNA Purification Mini Kit (Cat #55000, Norgen Biotek, Thorold, Canada) was added to the column and centrifuged for 1 minute at 2,000 RPM, followed by 2 minutes at 8,000 RPM.

Exosomal RNA was isolated from the exosomes isolated with ExoQuick-TC for Tissue Culture Media and Urine (System Biosciences, Mountain View, USA) using Norgen Biotek's Total RNA Purification Kit (Cat #17200, Norgen Biotek, Thorold, Canada) according to the manufacturer's recommendations.

Exosomal RNA was isolated from exosomes isolated with Total Exosome Isolation Reagent (from urine) (Life Technologies, Carlsbad, USA) using Life Technologies' Total Exosome RNA and Protein Isolation Kit (Cat #4478545, Life Technologies, Carlsbad, USA) according to the manufacturer's recommendations.

For analysis, the purified RNA was used as a template in qPCR reactions to amplify miR-30a, which is known to be a urinary exosomal miRNA. The initial reverse transcription was set up as follows:

3 µL exosomal RNA 0.5 µL 50 µM SLRT-miR-30a reverse primer 0.5 µL 10 mM dNTPs

4 µL 5×RT Buffer (TruScript Reverse Transcriptase Kit, Catalog #54440, Norgen Biotek, Thorold, Canada)

0.2 µL reverse-transcriptase 11.8 µL water

The reverse transcription was then run according to the following program using a BioRad CFX Connect:

Cycle 1: (1×) Step 1: 50.0° C. for 30:00

Cycle 2: (1×) Step 1: 70.0° C. for 10:00

Cycle 3: (1×) Step 1: 4.0° C. for 99:99

Next, the qPCR was set up as follows:

3 µL cDNA

10 µL 2×Syber Green Mix (Cat #170-8880, BioRad, Hercules, USA)

0.12 µL 50 µM miR-30a Forward Primer 0.12 µL 50 µM SLR Reverse Primer 6.76 µL water The qPCR was run according to the following program using a BioRad CFX Connect:

Cycle 1: (1×) Step 1: 95.0° C. for 03:00

Cycle 2: (40×) Step 1: 95.0° C. for 00:15

Step 2: 58.0° C. for 00:30

Step 3: 72.0° C. for 00:45

Data collection and real-time analysis enabled.

Cycle 3: (1×) Step 1: 57.0° C. for 01:00

Cycle 4: (80×) Step 1: 57.0° C. for 00:10

Increase setpoint temperature after cycle 2 by 0.5° C.

Melt curve data collection and analysis enabled.

Figure 6:
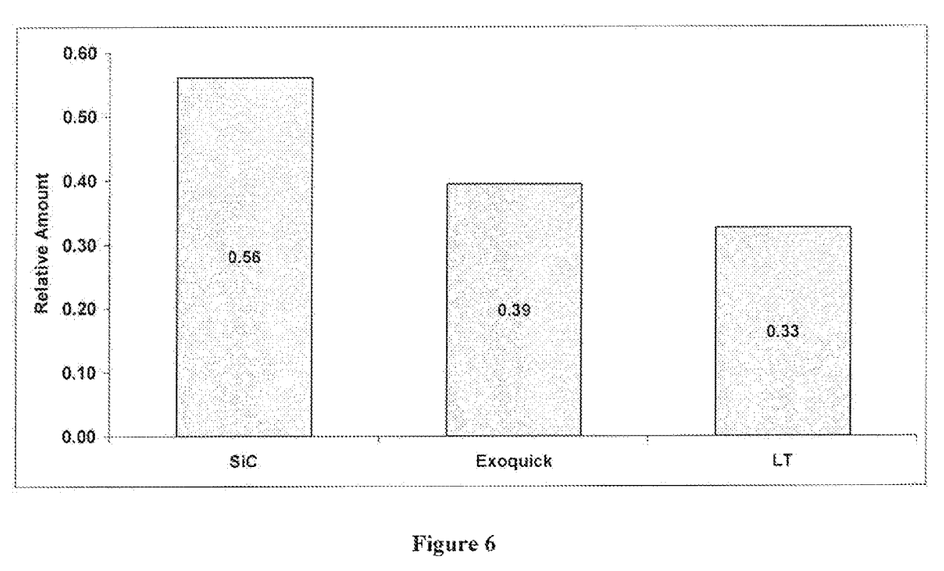
FIG. 6 is a bar graph showing the relative amount of exosomal RNA isolated from 5 mL of urine using SiC, ExoQuick-TC for Tissue Culture Media and Urine (System Biosciences, Mountain View, USA) and Total Exosome Isolation Reagent (from urine) (Life Technologies, Carlsbad, USA).

The resulting Ct values were then analyzed, and the relative amount of exosomal RNA isolated using each method was determined. As seen in FIG. 6, the SiC method resulted in the highest recovery of the urinary exosomal miRNA when compared to the other 2 methods.

Example 5

Comparing RNA Recovery from Exosomes Isolated Using SiC Versus Ultracentrifugation SiC in a slurry format was tested for its ability to isolate exosomes from increasing amounts of urine, and the performance of the SiC was compared to the traditional method of ultracentrifugation. The SiC slurry was prepared by adding 6.25 grams of SiC (G/S 2500) to 10 mL of 1×PBS (pH 7). One litre of urine was collected and processed as described in Example 3 above. Next, the SiC slurry was used to isolate the exosomes from 0.1 mL, 0.5 mL, 1 mL, 2.5 mL, 5 mL, 10 mL and 30 mL of the urine using the procedure described in Example 3.

Exosomes were also isolated from urine using traditional ultracentrifugation as outlined in Thery et al. (*Current Protocols in Cell Biology*, 2006).

RNA was then purified from the isolated exosomes. For exosomes purified using SiC, the RNA was isolated by adding 300 μL of Lysis Buffer from Norgen Biotek's Plasma/Serum RNA Purification Mini Kit (Cat #55000, Norgen Biotek, Thorold, Canada) and 37.5 μL of Lysis Additive from Norgen Biotek's Fatty Tissue RNA Purification Kit (Cat #36200, Norgen Biotek, Thorold, Canada), to the purified exosomes. This was mixed, then incubated at room temperature for 10 minutes. Next, 500 μL of ethanol was added and mixed well. This was then added to a column containing SiC resin, and centrifuged for 1 minute at 3,300×g (~6,000 RPM). The flowthrough was discarded, and the bound RNA was washed using Wash Solution from Norgen Biotek's Plasma/Serum RNA Purification Mini Kit (Cat #55000, Norgen Biotek, Thorold, Canada) by centrifugation for 30 seconds at 3,300×g (~6,000 RPM). The flowthrough was discarded, and the wash step was repeated 2 more times. After a dry spin, 50 μL of Elution Solution from Norgen Biotek's Plasma/Serum RNA Purification Mini Kit (Cat #55000, Norgen Biotek, Thorold, Canada) was added to the column and centrifuged for 1 minute at 2,000 RPM, followed by 2 minutes at 8,000 RPM.

Exosomal RNA was isolated from the exosomes isolated by centrifugation using Norgen's Total RNA Purification Kit (Cat #17200, Norgen Biotek, Thorold, Canada) according to the manufacturer's recommendations.

For analysis, the purified RNA was used as a template in qPCR reactions to amplify miR-30a, which is known to be a urinary exosomal miRNA. The initial reverse transcription was set up as follows:
 3 μL exosomal RNA
 0.5 μL 50 μM SLRT-miR-30a reverse primer
 0.5 μL 10 mM dNTPs
 4 μL 5×RT Buffer (TruScript Reverse Transcriptase Kit, Catalog #54440, Norgen Biotek, Thorold, Canada)
 0.2 μL reverse-transcriptase
 11.8 μL water The reverse transcription was then run according to the following program using a BioRad CFX Connect:
 Cycle 1: (1×) Step 1: 50.0° C. for 30:00
 Cycle 2: (1×) Step 1: 70.0° C. for 10:00
 Cycle 3: (1×) Step 1: 4.0° C. for 99:99

Next, the qPCR was set up as follows:
 3 μL cDNA
 10 μL 2×Syber Green Mix (Cat #170-8880, BioRad, Hercules, USA)
 0.12 μL 50 μM miR-30a Forward Primer
 0.12 μL 50 μM SLR Reverse Primer
 6.76 μL water The qPCR was run according to the following program using a BioRad CFX Connect:
 Cycle 1: (1×) Step 1: 95.0° C. for 03:00
 Cycle 2: (40×) Step 1: 95.0° C. for 00:15
  Step 2: 58.0° C. for 00:30
  Step 3: 72.0° C. for 00:45
 Data collection and real-time analysis enabled.
 Cycle 3: (1×) Step 1: 57.0° C. for 01:00
 Cycle 4: (80×) Step 1: 57.0° C. for 00:10
 Increase setpoint temperature after cycle 2 by 0.5° C.
 Melt curve data collection and analysis enabled.

Figure 7:
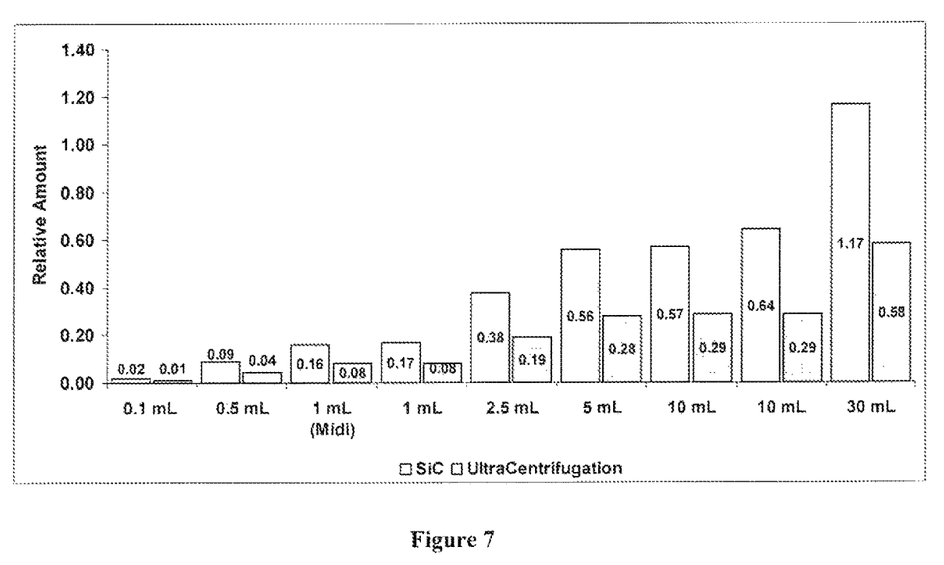
FIG. 7 is a bar graph showing the relative amount of exosomal RNA isolated from increasing amounts of urine using SiC and ultracentrifugation.

The resulting Ct values were then analyzed, and the relative amount of exosomal RNA isolated from each volume of urine using SiC and ultracentrifugation was determined. As can be seen in FIG. 7, the SiC method resulted in the highest recovery of the urinary exosomal miRNA at each volume tested when compared to ultracentrifugation.

The invention claimed is:

1. A method for producing a liquid sample substantially depleted of extracellular vesicles, the method comprising the steps of:
   (a) adjusting the pH of a liquid sample comprising extracellular vesicles to a preselected, binding pH;
   (b) contacting the liquid sample with silicon carbide, wherein at the preselected, binding pH, the extracellular vesicles bind to the silicon carbide;
   (c) separating the silicon carbide with the bound extracellular vesicles from the liquid sample to yield a liquid substantially depleted of extracellular vesicles; and
   (d) collecting the liquid substantially depleted of extracellular vesicles.

2. The method of claim 1, wherein the extracellular vesicles comprise exosomes.

3. The method of claim 1, wherein the liquid sample comprises a serum.

4. The method of claims 1, wherein the silicon carbide is in a slurry format or the silicon carbide is packed into a solid support column.

5. The method of claim 4, wherein the silicon carbide is a slurry format and wherein step (b) occurs before step (a), such that a liquid sample is contacted with the silicon carbide before the pH of the liquid sample is adjusted to the preselected binding pH to affect binding of the extracellular vesicles to the silicon carbide.

6. The method of claims 4, wherein the silicon carbide is a slurry format and wherein the silicon carbide is removed from the liquid sample by centrifugation or by gravity settling.

7. The method of claim 1, wherein the preselected, binding pH is about 2 to about 4.

8. The method of claim 7, wherein the preselected, binding pH is about 3.

9. The method of claim 1, wherein the preselected, binding pH is about 7 to about 11.

10. The method of claim 9, wherein the preselected, binding pH is about 8.5.

* * * * *